United States Patent [19]

Wilkins, Jr.

[11] Patent Number: 5,951,992
[45] Date of Patent: *Sep. 14, 1999

[54] LIMONENE PESTICIDES

[76] Inventor: Joe Sam Wilkins, Jr., 1706 E. Southmore, Pasadena, Tex. 77502

[ * ] Notice: This patent is subject to a terminal disclaimer.

[21] Appl. No.: 08/147,085

[22] Filed: Nov. 3, 1993

Related U.S. Application Data

[63] Continuation of application No. 07/788,937, Nov. 7, 1991, abandoned.

[51] Int. Cl.⁶ .............................. A01N 25/04; A01N 27/00
[52] U.S. Cl. ........................... 424/405; 424/406; 514/762; 514/763
[58] Field of Search ...................... 424/405, 406, 424/195.1; 514/762, 763; 585/600, 601

[56] References Cited

U.S. PATENT DOCUMENTS

| | | | |
|---|---|---|---|
| 4,379,168 | 4/1983 | Dotolo | 424/356 |
| 4,616,036 | 10/1986 | Hodgin | 514/470 |
| 4,891,222 | 1/1990 | Eichhoefer | 424/196.1 |
| 4,933,371 | 6/1990 | Hink et al. | 514/739 |

OTHER PUBLICATIONS

J. Med. Ent. vol. 11, No. 5: 617–621; Sharma et al. Orientation and Developmental inhibition in the Housefly by Certain Terpenoids.

Vet Hum Toxicol 30 (3) Jun. 1988; Powers et al.; an Evaluation of the Acute Toxicity of an Insecticidal Spray Containing.

*Primary Examiner*—Neil S. Levy
*Attorney, Agent, or Firm*—Laura G. Barrow

[57] ABSTRACT

Disclosed are novel methods for the use of pesticide formulations, containing d-limonene, directed against ants, termites, chinch bugs, sod web worms (*Bacillus thuringiensis*), weeds and the like.

5 Claims, No Drawings

LIMONENE PESTICIDES

This application is a continuation of Ser. No. 07/788,937, filed Nov. 7, 1991.

BACKGROUND OF THE INVENTION

1. Field of the Invention

The present invention relates to methods of using certain formulations containing d-limonene as a pesticide directed against ants, termites, chinch bugs, sod web worms (*Bacillus thuringiensis*), weeds and the like. More particularly, the present invention relates to methods of using certain formulations containing d-limonene as a pesticide for the treatment and control of the above referenced pests.

2. Description of the Prior Art

The use of pesticides to control insect pests and other destructive life forms is an area of increasing concern given that most pesticides are not only toxic to the pest against which they are directed but also are often toxic toward man, other animals and even crops for which they were designed as protection.

Certain naturally occurring pesticides have, however, proven to be safe to humans, animals and crops whom they are to benefit. Among the naturally occurring pesticides are a group belonging to the terpene family. Terpenes are widely distributed in nature, and occur in nearly all living plants. It is generally recognized that the term terpene not only applies to isoprene oligomers, but also to their saturated or partially saturated isomers, as well as to their derivatives, which are referred to as terpenoids, such as, for example, alcohols, aldehydes, esters, etc. Terpenes have been widely used as flavor and perfume materials. Common terpenes include turpentine, linalool and limonene. Limonene is a naturally occurring chemical found in high concentrations in citrus fruits and spices. In addition to uses as flavor additives and perfume materials, Limonene has been used in household and industrial cleaning products.

Certain terpenes have been found to have some insecticidal activity. Borneol, alpha terpineol, menthol linalool, and limonene have all been reported to posses insecticidal activity.

U.S. Pat. No. 4,379,168 discloses the use of D-Limonene as the insect killing ingredient in pesticides which are to be used as topical applications on small animals to kill fleas and ticks or as suitable for use in ridding household areas of cockroaches and other insects.

Certain pests directly affect blade crops, such as turf grasses, or are found inhabiting such environments. These insect pests can therefore cause extensive damage to the crops or can cause injury to workers handling the crops. Additionally, in the case of fire ants for example, such pests have proven to be a serious problem when they occupy grassy environments such as playgrounds, school campuses and pasture lands and grassing lands, and/or golf courses and other sports fields.

Yet another area where insect pests, in particular ants, have proven to be a major problem is in the area of electrical circuitry, in particular when such circuitry is subterranean. Since, ants tend to be attracted to electronic impulses, they have been found electrocuted within such circuits, as a result of this phenomenon ants have been determined to have been responsible for power outages, disruption of telephone signals, fouling of air conditioners, and the like.

A need exists to provide a pesticide which while demonstrating effective toxicity to the target pest is innocuous to the surrounding environment.

SUMMARY OF THE INVENTION

It is an object of the present invention to provide methods of treating pests which damage or reside on blade crops whereby the pests are eliminated without damage to the blade crop in specific or the overall environment in general.

It is another object of the present invention to provide methods of treating, school campuses, playgrounds, pasture lands, grassing lands, golf courses, sports fields and the like to control pest populations.

It is yet another object of the present invention to provide methods of controlling infestation of electronic circuitry.

DESCRIPTION OF THE PREFERRED EMBODIMENTS

The present invention relates to certain methods of using certain pesticide formulations containing D-Limonene, which pesticide formulations are directed against ants, termites, chinch bug, sod web worms (*Bacillus thuringiensis*), weeds and the like.

D-Limonene is a naturally occurring chemical found in high concentrations in citrus fruits and spices. In addition to uses as flavor additives and perfume materials, D-Limonene has been used in household and industrial cleaning products and is commonly available from commercial sources such as Florida Chemical Company, Inc. and is available in three different grades, named untreated/technical grade, food grade and lemon-lime grade. The food grade comprises about 97% d-limonene, the untreated/technical grade about 95%, and the lemon-lime grade about 70%, the balance in each case being other terpene hydrocarbons and oxygenated compounds.

Pesticide formulations useful in the practice of the present invention are formulations which can be used to treat pest infestation in grassy areas or blade crop areas including but not limited to turf farms, playgrounds, sports fields and the like, electronic circuitry and areas adjacent thereto, as well as household or commercial building infestations. In the case of applications where the infestation occurs in grassy areas or blade crop areas it is of significant importance that the grass, turf or blade crops themselves not be damaged to an appreciable degree. In the case of electronic circuitry, in particular when such circuitry is subterranean, it is of significant importance that the pesticide formulation be innocuous to the circuitry as well as innocuous to ground water.

In the use of these pesticide formulations several methods are preferentially used, these include a drench method, an injection method, a probe method, a spray method, and a fumigation method.

In the practice of the drench method, for example in the case of a fire ant mound, the pesticide formulation is applied to the external surface of the fire ant mound starting at the top center of the mound and proceeding in a circular pattern around the mound to its external periphery.

In the practice of the injection method, for example in the case of termite infestation, the pesticide formulation is directly injected under the slab of an affected dwelling.

In the practice of the probe method, for example in the case of a fire ant mound, a rod is used to enable the introduction of the pesticide formulation into the ant mound at a point below its surface.

In the practice of the spray method, the pesticide formulations may be sprayed onto a surface where the subject pest is visible.

In the practice of the fumigation method the pesticide formulations may be introduced into a building by means of a pesticide bomb resulting in the atmosphere of the building containing sufficient active ingredients to prove toxic to any pest found therein.

In the formulations useful in the practice of the present invention d-limonene is used as a pesticide along with surfactants or emulsifiers and water.

Any suitable emulsifier or surfactant can be used in the pesticide formulations useful in the practice of the present invention. Preferably, the emulsifier used is Mazclean EP available from PPG Industries, Inc.

The pesticide formulations useful in practice of the present invention may, preferably, range in the case of high potency formulations useful in commercial building, non-turf applications from about 99% d-limonene, 1% water with a sufficient amount of surfactant to accomplish solubilization of the water and limonene to about 20% d-limonene, 80% water with surfactant. The surfactant will preferably, in the latter case, be in a ratio of 2 parts surfactant to 3 parts d-limonene. In the case of lower potency formulations useful in commercial building, households and turf or grassy area applications the pesticide formulations may range from about 20% d-limonene, 80% water with surfactant preferably present in a ratio of 2 parts surfactant and 3 parts d-limonene, to formulations of about 3% d-limonene, 2% surfactant and 97% water.

In order to prepare the formulations useful in the practice of the invention the d-limonene is preferentially first blended with the surfactant and then the water is slowly added in order to achieve a solubilized mixture.

The following example is intended to illustrate an embodiment of the invention as described above and claimed hereafter and is not intended to limit the scope of the invention in any way.

EXAMPLE 1

A formulation consisting of 4 gallons of D-limonene and 0.66 gallons of Mazclean EP and 200 gallons of water is prepared. The formulation is then applied on 10 acres of turf or grassy area at a rate of 20 gallons per acre. The application is achieved by employing a commercial sprayer approximately 12 ft. long which is pulled behind a vehicle with a product tank, such as for example a grass farmer. Upon application of the above formulation the following pests were observed to have been eradicated: ants, sod web worms, and chinch bugs. The grass or turf was not affected by the treatment.

The present invention and the embodiments disclosed herein are well adapted to carry out the objective and obtain the ends set forth at the outset. Certain changes may be made to the above described methods and formulations to be used in said methods without departing from the spirit and the scope of this invention. It is realized that changes are possible and it is further intended that each element or step recited in any of the following claims to be understood as referring to all equivalent steps or elements for accomplishing substantially the same results in substantially the same or equivalent manner. It is intended to cover the invention broadly in whatever form its principles may be utilized.

I claim:

1. A method of effectively eradicating queen fire ants comprising:
    (a) applying a formulation to an area to be eradicated of queen fire ants, wherein said formulation consists of from about 2 to about 10 percent d-limonene, from about 2 to about 10 percent emulsifier, and from about 80 to about 96 percent water; and
    (b) allowing said formulation to remain in contact with said area for a suitable period of time to eradicate said queen fire ants.

2. The method of claim 1, wherein d-limonene comprises about 3 percent of said formulation, said emulsifier comprises about 3 percent of said formulation, and said water comprises about 94 percent of said formulation.

3. The method of claim 1, wherein the contacting is achieved by means of a drench method.

4. The method of claim 1, wherein the contacting is achieved by means of a spray method.

5. The method of claim 1, wherein the contacting is achieved by means of an injection method.

* * * * *